United States Patent
Novich et al.

(10) Patent No.: US 6,231,533 B1
(45) Date of Patent: May 15, 2001

(54) ORTHOPEDIC SPLINTING ARTICLE

(75) Inventors: Bruce E. Novich; Walter J. Robertson, both of Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/316,524

(22) Filed: May 21, 1999

(51) Int. Cl.$^7$ .................................................. A61F 5/00
(52) U.S. Cl. ........................................ 602/7; 602/5; 602/8
(58) Field of Search ............................ 602/5, 7, 8, 26, 602/27; 601/136

(56) References Cited

U.S. PATENT DOCUMENTS

| | | | |
|---|---|---|---|
| 3,373,741 | 3/1968 | Hill et al. | 128/90 |
| 3,997,306 | 12/1976 | Hedden | 65/3 C |

(List continued on next page.)

FOREIGN PATENT DOCUMENTS

| | | |
|---|---|---|
| 0 628 319 | 12/1994 | (EP) . |
| WO94/23678 | 10/1994 | (WO) . |
| WO94/25076 | 11/1994 | (WO) . |
| WO94/28837 | 12/1994 | (WO) . |
| WO95/26698 | 10/1995 | (WO) . |
| WO96/23531 | 8/1996 | (WO) . |
| WO97/03707 | 2/1997 | (WO) . |

OTHER PUBLICATIONS

*The Manufacturing Technology of Glass Fibres*, by K. L. Loewenstein (3rd Ed 1993) pp. 13–19, 293–311, pp. 30–44, 47–60, 115–122 and 126–135.

*The Manufacturing Technology of Glass Fibres*, by K. L. Loewenstein (3rd Ed 1993) p. 25, pp. 237–291, pp. 165–172.

*The Manufacturing Technology of Glass Fibres*, by K. L. Loewenstein (3rd Ed 1993) p. 219–222.

*Encyclopedia of Polymer Science and Technology*, vol. 6 (1967), pp. 505–712.

Product Information for Instron Corporation.

*Primary Examiner*—Michael A. Brown
*Assistant Examiner*—Lalita M. Hamilton
(74) *Attorney, Agent, or Firm*—Andrew C. Siminerio

(57) ABSTRACT

One aspect of the present invention is an orthopedic splint for temporarily supporting an injured body limb, comprising: a non-woven mat at least partially impregnated with a curable resin matrix material; a first resin impermeable layer extending along at least a portion of at least one major surface of the mat; a second resin impermeable layer extending along at least along a portion of an opposing major surface of the mat; and a curing agent permeable cover surrounding the mat and the first and second resin impermeable layers. In one particular embodiment of the invention, the resin matrix material comprises a moisture curable, ambient air dried resin matrix material, the mat comprises a needled mat comprising randomly oriented continuous glass fibers and having a weight, prior to resin impregnation, of between about 0.15 to about 2.44 kilograms per square meter, the first resin impermeable layer is a heat insulating layer, and the cover is a water permeable cover.

21 Claims, 1 Drawing Sheet

U.S. PATENT DOCUMENTS

| | | | |
|---|---|---|---|
| 4,277,531 | 7/1981 | Picone | 128/228 |
| 4,305,742 | 12/1981 | Barch et al. | 65/3.43 |
| 4,306,549 | 12/1981 | Canie | 128/90 |
| 4,433,680 | 2/1984 | Yoon | 128/90 |
| 4,442,833 | 4/1984 | Dahlen et al. | 128/90 |
| 4,498,467 * | 2/1985 | Kirkpatrick et al. . | |
| 4,502,479 | 3/1985 | Garwood et al. | 128/90 |
| 4,542,106 | 9/1985 | Sproull | 501/38 |
| 4,609,578 | 9/1986 | Reed | 428/76 |
| 4,615,717 | 10/1986 | Neubauer et al. | 65/4.4 |
| 4,668,563 | 5/1987 | Buese et al. | 428/230 |
| 4,692,375 | 9/1987 | Neubauer et al. | 428/299 |
| 4,705,840 | 11/1987 | Buckanin | 528/53 |
| 4,800,872 | 1/1989 | Buese et al. | 128/90 |
| 4,898,159 | 2/1990 | Buese et al. | 128/90 |
| 4,927,869 | 5/1990 | Dana et al. | 523/502 |
| 4,963,176 | 10/1990 | Bailey et al. | 65/4.4 |
| 5,007,418 | 4/1991 | Bartizal et al. | 128/90 |
| 5,027,803 | 7/1991 | Scholz et al. | 128/29 R |
| 5,088,484 * | 2/1992 | Freeman et al. . | |
| 5,169,698 | 12/1992 | Behjati et al. | 428/68 |
| 5,171,208 | 12/1992 | Edenbaum et al. | 602/6 |
| 5,342,291 | 8/1994 | Scholz et al. | 602/41 |
| 5,354,259 | 10/1994 | Scholz et al. | 602/8 |
| 5,437,928 | 8/1995 | Thimons et al. | 428/391 |
| 5,514,080 * | 5/1996 | Blott et al. . | |
| 5,527,266 | 6/1996 | Hiraishi et al. | 602/8 |
| 5,540,652 | 7/1996 | Callinan et al. | 602/1 |
| 5,620,095 | 4/1997 | Delmore et al. | 206/438 |
| 5,755,678 | 5/1998 | Parker et al. | 602/6 |
| 5,789,329 | 8/1998 | Eastes et al. | 501/36 |
| 5,843,354 * | 12/1998 | Evan et al. . | |
| 5,879,778 * | 3/1999 | Barnes . | |

* cited by examiner

ORTHOPEDIC SPLINTING ARTICLE

BACKGROUND OF THE INVENTION

1. Field of the Invention

This invention relates generally to temporary support for injured limbs, and in particular to the use of glass fiber mat in orthopedic splints.

2. Technical Considerations and Prior Art

Methods of immobilizing broken, fractured, sprained or strained limbs so that they can heal over a period of time typically include the use of porous fabrics that are coated or impregnated with plaster of paris or curable resins. At the time of an accident, it is advantageous to temporarily immobilize the injured limb to prevent any further injury, for example by using a splint, until a more "permanent" immobilizer can be used to set the limb. The splint must provide sufficient strength to immobilize and if necessary support the injured limb but should also be easily removable. It would also be beneficial if the splint could mold to at least a portion of the limb so as to provide more comfortable support. Generally, such temporarily immobilizing systems typically include splints having multiple layers of resin impregnated woven fabric which remains stable when maintained in substantially moisture-free conditions but hardens quickly upon exposure to sufficient moisture to form a rigid self-supporting structure.

U.S. Pat. No. 4,306,549 discloses a splint arrangement that includes a woven fiberglass mat strip enclosed within a vacuum envelope. A curable hardening agent is injected into the envelope and absorbed by the woven mat. Prior to hardening, the splint is wrapped around the injured limb as a bandage to provide support.

U.S. Pat. Nos. 4,609,578; 4,668,563 and 4,800,872 disclose orthopedic casting systems that use curable resin coated fiberglass tapes that can harden and form a rigid support structure.

U.S. Pat. Nos. 5,027,803 and 5,755,678 disclose splinting and support bandages that incorporate multiple layers of woven or knitted fiberglass fabric impregnated with a reactive system that hardens when exposed to moisture.

It would be advantageous to provide a splint that incorporates a single resin impregnated layer having sufficient strength that it can support and temporarily immobilize an injured limb before conventional longer term immobilization of the limb is employed.

SUMMARY OF THE INVENTION

One aspect of the present invention is an orthopedic splint for temporarily supporting an injured body limb, comprising: a non-woven mat at least partially impregnated with a curable resin matrix material; a first resin impermeable layer extending along at least a portion of at least one major surface of the mat; a second resin impermeable layer extending along at least along a portion of an opposing major surface of the mat; and a curing agent permeable cover surrounding the mat and the first and second resin impermeable layers. In one particular embodiment of the invention, the resin matrix material comprises a moisture curable, ambient air dried resin matrix material, the mat comprises a needled mat comprising randomly oriented continuous glass fibers and having a weight, prior to resin impregnation, of between about 0.15 to about 2.44 kilograms per square meter, the first resin impermeable layer is a heat insulating layer, and the cover is a water permeable cover.

Another aspect of the present invention is an orthopedic splint for temporarily supporting an injured body limb, comprising: a non-woven mat at least partially impregnated with a curable resin matrix material; and a curing agent permeable cover surrounding the mat, the cover comprising: a first portion which overlays at least a portion of a first major surface of the mat and provides a first resin impermeable barrier; and a second portion which overlays at least a portion of an opposing second major surface of the mat and provides a second resin impermeable barrier.

Still another aspect of the present invention is a method of making an orthopedic splint for temporarily supporting an injured body limb, comprising the steps of: impregnating a nonwoven mat with a moisture curable, ambient air dried resin matrix material; overlaying at least a portion of a first major surface of the mat with a first resin impermeable barrier; overlaying at least a portion of an opposing second major surface of the mat with a second resin impermeable barrier; and enclosing the mat and the first and second barriers within a curing agent permeable cover.

Yet another aspect of the present invention is a method of immobilizing a body limb comprising the steps of activating the curable resin matrix system in a splint as discussed above, applying the splint to the body limb, molding the splint to the shape of at least a portion of the body limb, temporarily securing the splint to the body limb, and allowing the resin system to cure.

DETAILED DESCRIPTION OF THE INVENTION

Figure 1:
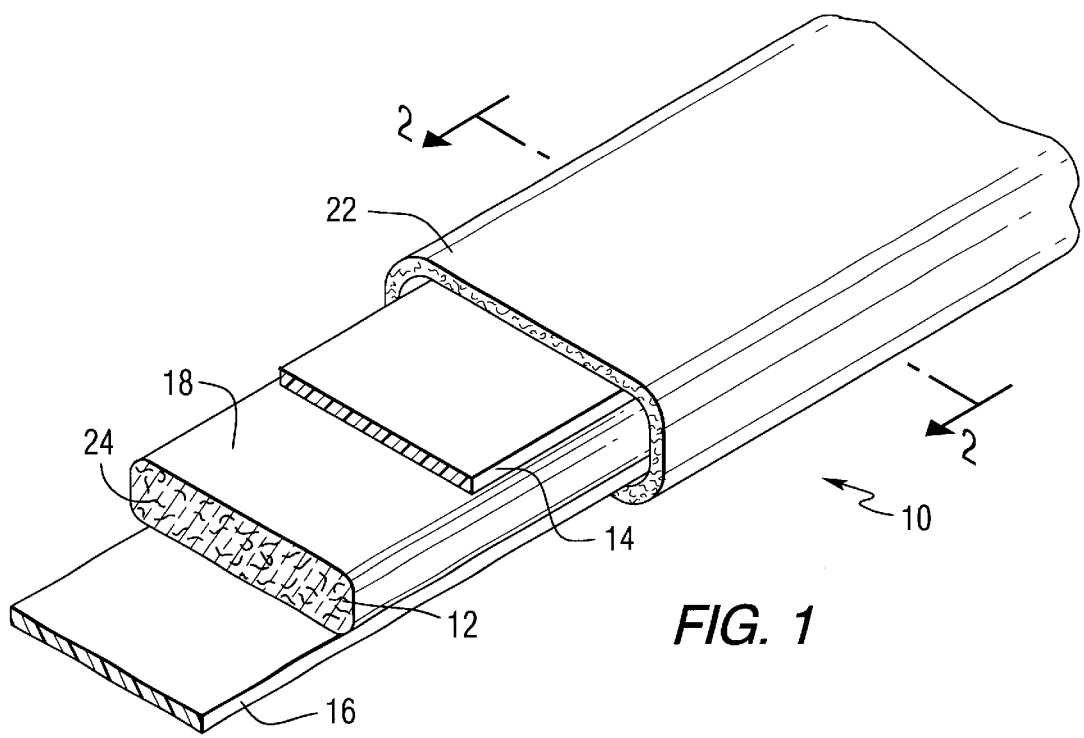
FIG. 1 is an isometric view of an orthopedic splint incorporating features of the present invention.

The present invention relates to an orthopedic splinting article that is strong, lightweight and shippable. Referring to FIG. 1, the splint 10 generally comprises a flexible substrate 12 that is impregnated with a curable resin matrix, resin impermeable layers 14 and 16 extending along opposing surfaces 18 and 20 of substrate 12, respectively, to help contain the resin during storage and curing, and a curing agent permeable cover 22 that surrounds the substrate 12, layers 14 and 16 and holds the splint 10 together. As used herein, the term "curable resin matrix" includes resins that harden and resist deformation as a result of a chemical reaction, e.g. a crosslinking reaction, as well as resins that coalesce to form a substantially continuous film after removal of water or some other carrier. The resin used to impregnate the substrate 12, as will be discussed later in more detail, is generally sticky in nature and will also tend to hold the components of the splint 10 together.

In the present invention, the substrate 12 is a fiber mat 24 impregnated with a suitable resin matrix, and preferably a glass fiber mat. The resin matrix preferably exhibits the following properties: (1) substantial storage life, (2) low toxicity, (3) appropriate viscosity and flow characteristics that allow it to coat and impregnate the mat and maintain mat coverage while in storage and during curing but not so high that the mat is unduly hard, (4) fast cure rate, i.e. set up preferably within about 10 to about 15 minutes, preferably within about 3 to about 5 minutes, to the shape of the body part and cure to form a weight bearing splint sufficiently strong to support an injured limb within a period of about 30 minutes to several hours, (5) cure without generation of substantial heat that can harm the limb, (6) minimal or nonoffensive odor, (7) free of offensive or noxious organic solvents, (8) reasonable work life such that there is a reasonable period of time in which to mold the material to the shape of the limb, (9) reasonable flexibility in the uncured state such that the material readily assumes the shape of the limb during application and (10) does not cause chemical irritation of the skin. Although not limiting in the present invention, the resin matrix is preferably a moisture curable, preferably water cured, air dried, thermosetting matrix, and more preferably an isocyanate containing resin system, although non-isocyanate resin systems are also available. Examples of resin systems that can be used in the present invention include but are not limited to those disclosed in U.S. Pat. No. 4,433,680 (see column 4 line 63 through column 6 line 40), U.S. Pat. No. 4,502,479 (see column 9 line 18 through column 15 line 32), U.S. Pat. No. 4,705,840 (see column 12 line 39 through column 18 line 64), U.S. Pat. No. 5,007,418 (see column 8 line 31 through column 15 line 29), U.S. Pat. No. 5,169,698 (see column 5 line 60 through column 8 line 42), and U.S. Pat. No. 5,540,652 (see column 19 line 45 through column 25 line 14), and WO 94/25076 (see page 5 line 30 through page 7 line 2), which is hereby incorporated by reference.

As used herein, the term "maf" means a non-woven fabric comprising chopped and/or continuous fibers and/or fiber strands, and in particular, chopped glass fiber strands and/or continuous glass fiber strands. This type of material is sometimes referred to as felt. More specifically, chopped glass fiber strand mat is a non-woven product produced by randomly depositing chopped glass fiber strands on a horizontal surface and binding the chopped strands together with a suitable chemical binder. Although not limiting in the present invention, the chopped strands are typically from about 20 to about 50 millimeters long. Continuous glass fiber strand mat is a non-woven product comprising interleaved layers of generally continuous glass fiber strand. The strands are bound together by a suitable chemical binder and/or are mechanically consolidated, for example by a needling operation wherein barbed needles penetrate the glass fiber layers of the mat and intermingle strands between the various layers as is well known to those skilled in the art. Some mat configurations combine chopped glass fiber strands with continuous glass fiber strands. In addition, roving, and in particular glass fiber roving, as well as woven and/or non-woven fabrics can be included as a secondary component of the mat construction, and in particular glass fiber fabrics, can also be incorporated into the mat structure. Other mat configurations include shredded fiber strands. Such combinations of components are considered to be within the broad definition of 'mat' as used herein. For additional information with respect to typical glass fiber mat designs and useful equipment and processes for forming mats, see K. Loewenstein, *The Manufacturing Technology of Continuous Glass Fibres*, (3rd edition 1993) at pages 13–19 and 293–311, and U.S. Pat. No. 4,277,531 (see column 3, line 37 through column 4, line 54), U.S. Pat. No. 4,615,717 (see column 5, line 16 through column 7, line 12); and U.S. Pat. No. 4,963,176 (see column 11, line 31 through column 14, line 11), which teachings are hereby incorporated by reference. Although not limiting in the instant invention, it is preferred that mat 24 be a needled continuous glass fiber strand mat. Non-limiting examples of the types of mats that can be used in the present invention include needled mat having randomly oriented continuous glass fibers, such as but not limited to ZETAMA™ 1020 and 1030 mat, and needled mat having randomly oriented continuous glass fibers and unidirectional roving, such as but not limited to ZETAMAT™ 2056 and 2078 mat and PPG mat product code 5293470056, all commercially available from PPG Industries, Inc.

The mat 24 comprises glass fibers based upon oxide compositions such as silicates selectively modified with other oxide and nonoxide compositions. Useful glass fibers can be formed from any type of fiberizable glass composition known to those skilled in the art and include those prepared from fiberizable glass compositions such as "E-glass", "A-glass", "C-glass", "D-glass", "R-glass", "S-glass" and E-glass derivatives. As used herein "E-glass derivatives" means glass compositions that include minor amounts of fluorine and/or boron and preferably are fluorine-free and/or boron-free. Furthermore, as used herein "minor" means less than about 1 weight percent fluorine and less than about 5 weight percent boron. Preferred glass fibers are formed from E-glass and E-glass derivatives. Such compositions and methods of making glass filament therefrom are well known to those skilled in the art and further discussion thereof is not believed necessary in view of the present disclosure. If additional information is needed, such glass compositions and fiberization methods are disclosed in Loewenstein at pages 3044, 47–60, 115–122 and 126–135, and U.S. Pat. No. 4,542,106 (see column 2, line 67 through column 4, line 53) and U.S. Pat. No. 5,789,329 (column 2, line 65 through column 4, line 24), which are hereby incorporated by reference.

The glass fibers of mat 24 can have a nominal filament ranging from about 5.0 to about 35.0 micrometers (corresponding to a filament designation of D through U and above) and preferably have a nominal filament diameter ranging from about 5.0 to about 24.0 micrometers. For further information regarding nominal filament diameters and designation of glass fibers, see Loewenstein at page 25, which is hereby incorporated by reference.

Referring now to FIG. 1, the glass fiber strands forming mat 24 are coated on at least a portion of their outer surfaces with at least a partial layer comprising at least a partially dried residue of a coating composition which is compatible with a resin matrix material. As used herein, the phrase "compatible with the resin matrix material" means that the components of the coating composition facilitate wet-through and wet-out of the matrix material upon the fibers forming strands in mat 24 and provide adequate physical properties after curing. The measure of the penetration of the matrix material through the mat 24 is referred to as "wet-through". The measure of the flowability of the matrix material through the glass fiber mass to obtain essentially complete encapsulation of the entire surface of each glass fiber by the matrix material is referred to as "wet-out".

Suitable coating compositions include sizing compositions and/or secondary coating compositions. As used herein, the terms "size", "sized" or "sizing" refer to the composition applied to the fibers immediately after formation of the glass fibers. The term "secondary coating" refers to a coating composition applied secondarily to one or a plurality of strands after the sizing composition is applied, and preferably at least partially dried.

The sizing composition preferably comprises one or more polymeric film forming materials that are compatible with a thermosetting matrix material. Suitable polymeric film-forming materials include thermosetting materials, thermoplastic materials, and mixtures thereof.

The sizing composition can additionally include one or more thermoplastic vinyl polymers, such as polyvinyl pyrrolidones, in an amount that does not detrimentally affect the compatibility of the polymeric film forming materials discussed above with the thermosetting matrix material. Examples of suitable polyvinyl pyrrolidones include PVP K-15, PVP K-30, PVP K-60 and PVP K-90, each of that are commercially available from ISP Chemicals of Wayne, N.J.

The sizing composition preferably further comprises one or more glass fiber lubricants that are chemically different from the polymeric film-forming materials discussed above. Useful glass fiber lubricants include cationic, non-ionic or anionic lubricants and mixtures thereof.

The sizing composition preferably comprises one or more coupling agents selected from the group consisting of organo silane coupling agents, transition metal coupling agents (such as titanium, zirconium and chromium coupling agents), amino-containing Werner coupling agents and mixtures thereof. Examples of suitable coupling agents include epoxy, glycidoxy, mercapto, cyano, allyl, alkyl, urethano, halo, isocyanato, ureido, imidazolinyl, vinyl, acrylato, methacrylato, amino or polyamino group containing materials. Non-limiting examples of suitable coupling agents include Z-6040 gamma-glycidoxypropyltrimethoxysilane (commercially available from Dow Coming), A-187 gamma-glycidoxypropyltrimethoxysilane, A-174 gamma-methacryloxypropyltrimethoxysilane and A-100 gamma-aminopropyltriethoxysilane silane coupling agents (each of which are commercially available from OSi Specialties, Inc. of Tarrytown, N.Y.).

Crosslinking materials can also be included in the sizing composition. Non-limiting examples of suitable crosslinkers include melamine formaldehyde, blocked and unblocked isocyanates, polyesters and polyamides.

The sizing composition can include one or more emulsifying agents for emulsifying components of the sizing composition. Non-limiting examples of suitable emulsifying agents or surfactants include polyoxyalkylene block copolymers, ethoxylated alkyl phenols, polyoxyethylene octylphenyl glycol ethers, ethylene oxide derivatives of sorbitol esters and polyoxyethylated vegetable oils.

The sizing composition can also include one or more aqueous dispersible or soluble plasticizers to improve flexibility. Examples of suitable non-aqueous-based plasticizers that are aqueous dispersible plasticizers include phthalates, trimellitates and adipates.

Fungicides, bactericides and anti-foaming materials and organic and/or inorganic acids or bases in an amount sufficient to provide the aqueous sizing composition with a pH of about 2 to about 10 can also be included in the sizing composition.

Water (preferably deionized) is included in the sizing composition in an amount sufficient to facilitate application of a generally uniform coating upon the strand.

The sizing composition can also include other materials well known to those skilled in the art.

Non-limiting examples of sizing compositions that can be used in the present invention are disclosed in U.S. Pat. No. 3,997,306 (see column 4, line 60 through column 7, line 57); U.S. Pat. No. 4,305,742 (see column 5, line 64 through column 8, line 65) and U.S. Pat. No. 4,927,869 (see column 9, line 20 through column 11, line 19), and U.S. patent application Ser. No. 081787,735 (see page 7, line 1 through page 12, line 13 and page 28, line 15 through page 39 line 10) and Ser. No. 08/984,429 (see page 10, line 1 through page 15, line 17), which are hereby incorporated by reference. Additional information and further non-limiting examples of suitable sizing compositions are set forth in Loewenstein at page 237–291, which is hereby incorporated by reference.

The sizing can be applied in many ways, for example by contacting the filaments with a static or dynamic applicator, such as a roller or belt applicator, spraying or other means. For a discussion of suitable applicators, see Loewenstein at pages 165–172, which is hereby incorporated by reference.

The sized fibers are dried at room temperature or at elevated temperatures to remove excess moisture from the fibers and cure any curable sizing or secondary coating composition components. Drying of glass fiber forming packages or cakes is discussed in detail in Loewenstein at pages 219–222, which is hereby incorporated by reference. For example, a forming package can be dried in an oven at a temperature of about 104° C. (220° F.) to about 160° C. (320° F.) for about 10 to about 24 hours to produce glass fiber strands having an at least partially dried residue of the coating composition thereon. The temperature and time for drying the glass fibers will depend upon such variables as the percentage of solids in the sizing composition, components of the sizing composition, type of glass fiber, and moisture content. The sizing composition is preferably present on the fiber in an amount ranging from about 0.3 percent to about 2.5 percent by weight after drying, and preferably about 0.5 to about 1.5 percent by weight, measured by loss on ignition.

Alternatively, the coating composition can be an impregnating or secondary coating having components such as are discussed above which are applied to at least a portion of the surface of the strands in an amount effective to coat or impregnate the portion of the strands. The secondary coating can be conventionally applied by methods well known in the art, for example by dipping the strand in a bath containing the composition, by spraying the composition upon the strand or by contacting the strand with a static or dynamic applicator such as a roller or belt applicator. The coated strand can be passed through a die to remove excess coating from the strand and/or dried, as discussed above, for a time sufficient to at least partially dry and/or cure the secondary coating.

In an alternative embodiment of the invention, in addition to the glass fibers, mat 24 can further comprise fibers or strands of materials other than glass fibers ("non-glass fibers"). Suitable non-glass fibers believed to be useful in the present invention are discussed at length in the *Encyclopedia of Polymer Science and Technology*, Vol. 6 (1967) at pages 505–712, and U.S. Ser. No. 08/828,212 at page 15, line 21 through page 17, line 10, which are hereby incorporated by reference.

The resin matrices that can be used in combination with the present invention can be applied to impregnate the mat 24 using techniques well known in the art. For example and not limiting in the instant invention, impregnation can be carried out by immersing the mat into the resin and removing excess material as disclosed in U.S. Pat. No. 5,169,698 (see column 4, lines 16–35). After applying the resin matrix, the splint 10 can be assembled and sealed in an air and moisture tight bag, as will be discussed later, to prevent premature curing of the resin. If desired, prior to splint assembly, the resin-coated mat can further processed to ensure that the entire mat is thoroughly impregnated with resin. For example, and without limiting the present invention, the coated mat can be sealed in an air and moisture-tight bag and held in order to allow the resin to wick throughout the mat 24.

Layer 14 provides as a resin impermeable barrier to protect the injured limb from contacting the resin. If desired, it can also provide a cushion between the mat 24 and the injured limb. Depending on the resin matrix system, curing of the resin can generate heat. If such a resin matrix system is used, layer 14 will further function as a heat-insulating layer during curing of the resin impregnated mat 24. In the non-limiting embodiment of the invention shown in FIGS. 1 and 2, layer 14 is loosely positioned at least along a portion of upper surface 18 of mat 24, although layer 14 can be incorporated into the splint 10 in other forms as will be discussed later.

Layer 16 provides as a resin impermeable barrier that protects the individual forming and applying the splint 10 from the activated resin. In addition, layer 16 is configured to allow the resin in the mat 24 to be activated. For example and without limiting in the present invention, if curing agent for the resin system is water, the layer 16 is configured to allow water to saturate the resin-impregnated mat 24 and activate the resin. More particularly, in the embodiment illustrated in FIGS. 1 and 2, layer 16 is loosely positioned at least along a portion of the lower surface 20 of mat 24. The interface between the upper surface 18 of the mat 24 and the insulating layer 14 is generally not covered by the layer 16 so as to allow water to enter and soak the mat 24 and activate the resin. In addition, water can enter the mat 24 through the longitudinally extending, exposed edges 26 of the mat 24, as well as through lower mat surface 20 along the layer 16/mat 24 interface. If desired, portions of the layer 16 can be loosely wrapped around the edges 26 and/or the leading and trailing edges of the mat 24 to further enclose the resin impregnated mat 24.

Figure 2:
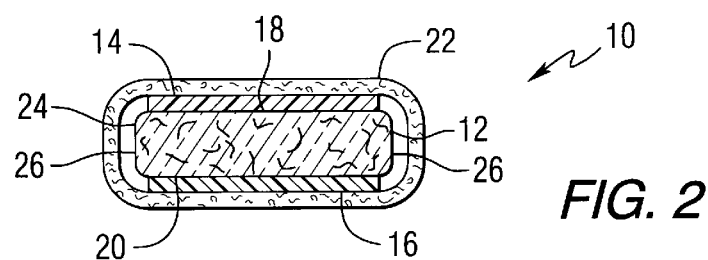
FIG. 2 is a sectional view taken along line 2—2 of FIG. 1.

Although not limiting in the present invention, in the particular embodiment illustrated in FIGS. 1 and 2, depending on their required functions, the layers 14 and 16 can be a polyvinylchloride, polyethylene, polyester, polyether, ethylene vinyl acetate, and flexible foams produced from material such as but not limited to polychloroprene, silicone rubber, polyolefins, polyethylene or polyurethane.

As discussed earlier, cover 22 encloses the components of the splint 10 and makes the splint 10 easier to handle. In addition, the cover must be designed to allow the curing agent to pass through the cover 22 so that the curing agent can combine with the resin. For example and without limiting the present invention, in instances where the resin matrix system is water activated, the cover 22 should be water permeable so as to allow the water to enter the splint 10, and more specifically mat 24, through the cover 22. It should also be appreciated that with a curable resin matrix that cures by coalescing after removal of water or some other carrier, curing agent permeable cover 22 should be permeable in a manner that allows the water to leave the splint 10. Non-limiting examples of materials suitable for cover 22 include, but are not limited to, water permeable microporous woven, non-woven, knitted or melt blown layers such as weft knitted tubular fabric, knitted stockinette, non-woven polymeric webs, and various natural and synthetic woven fabrics. Non-limiting examples of non-woven polymeric webs include polyesters, polyurethanes, nylons, polyolefins, and foams. Non-limiting examples of natural and synthetic woven fabrics include cotton or synthetic polymeric fabrics such as polyesters, nylons and the like including spun-laced fabrics. These materials are preferably provided in a configuration that facilitates conformability. Cover 22 preferably has a knitted sleeve construction. As an alternative, cover 22 can be a fabric that is wrapped around the splint components.

Although not required, it is expected that the splint 10 be from about 5.1 cm (about 2 inches) to about 10.2 cm (about 4 inches) wide by about 30.5 cm (about 12 inches) long, although longer and wider splints are contemplated. In addition, the weight of the mat 24 portion of the splint 10 (after needling but prior to resin impregnation) is preferably between about 0.16 to about 2.62 kilograms per square meter (about 0.5 to about 8 ounces per square foot), more preferably about 0.32 to about 1.97 kilograms per square meter (about 1 to about 6 ounces per square foot), and most preferably about 0.66 to about 1.31 kilograms per square meter (2 to about 4 ounces per square foot).

As discussed earlier, after the mat 24 is impregnated with the resin matrix, the splint 10 is assembled and sealed within an air and moisture tight container or bag (not shown) to prevent premature curing of the resin. Typically, such bags are hermetically sealed pouches formed from metal foil or metallized plastic layers as disclosed in U.S. Pat. No. 5,620,095 (see column 4 lines 27–60) and WO 94/28837 (see page 14 line 7 through page 16 line 11).

In practice, to immobilize an injured limb, the splint 10 is removed from the sealed bag and the resin is activated. In the embodiment of the invention where the resin is water activated, the splint 10 is wetted, for example by submerging the splint 10 in water or by positioning the splint 10 under a running faucet to soak the impregnated mat 24. The splint 10 can be squeezed to remove air bubbles entrapped within the mat 24 and ensure that the mat 24 is thoroughly saturated. The splint 10 is then held against the injured limb in a manner that supports the limb, with layer 14 facing the limb. The mat 24 of the splint 10 is then formed to conform to the limb. If desired, the splint 10 can be preformed prior to application against the limb. When formed, the splint 10 is secured to the limb, for example by tape or an elastic bandage. If desired, a second splint can be applied to the opposite side of the limb. Both splints are then secured to the injured limb to better immobilize the limb.

Referring to FIG. 2, as the mat 24 of the splint 10 cures and dries, loose fibers along the edges 26 of the mat 24 can harden in a manner that results in a rough, abrasive edge. In order to avoid this condition, the mat can be configured such that the edges 26 are not positioned along the sides of the splint 10. More specifically, referring to FIG. 3, splint 110 includes a mat 124, resin impermeable layers 114 and 116 and a cover 122. Mat 124 includes cut edges 128 that are folded inwardly such that the edges 128 lie along a central portion 130 of the mat 124. If desired, the edges 128 can be positioned such that they abut each other. Although not required, it is preferred that the mat 124 be oriented such that the edges 128 are overlaid by layer 114 so as to ensure that there are no roughened edges or sides along the splint that can irritate the injured party. With this configuration, water can still enter and soak the mat 124 to activate the resin matrix system through folded edges 126 of the mat 124. It should be appreciated that with the folded mat configuration shown in FIG. 3 and discussed above, the weight of the mat 124 can be reduced such that the effective weight of the mat, i.e. a double layer of the mat 124 is preferably between about 0.15 to about 2.44 kilograms per square meter (about 0.5 to about 8 ounces per square foot), more preferably from about 0.31 to about 1.83 kilograms per square meter (about 1 to about 6 ounces per square foot), and most preferably about 0.61 to about 1.22 kilograms per square meter (about 2 to about 4 ounces per square foot).

Figure 3:
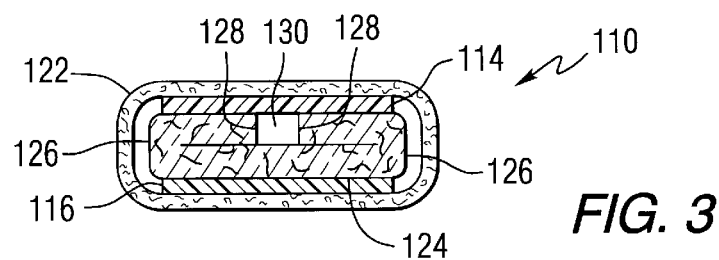
FIGS. 3 and 4 are views similar to FIG. 2 illustrating alternate embodiments of the invention.
Figure 4:
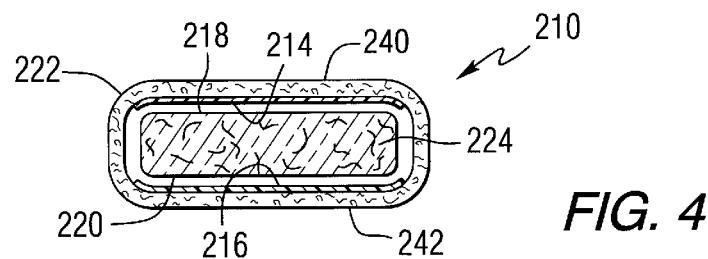

Although the particular embodiments of the invention illustrated in FIGS. 1–3 show the layers 14, 16, 114 and 116, and covers 22 and 122 as separate elements, it is contemplated that these features of the present invention can be integrated into a single member. More specifically, referring to FIG. 4, cover 222 of splint 210 is a sleeve member. Portion 240 of cover sleeve 222, which overlays surface 218 of mat 224 and contacts the injured limb, is provided with an barrier layer 214 having properties of the type discussed earlier in connection with layer 14, and portion 242 of cover sleeve 222, which overlays surface 220 of mat 224, is provided with a barrier layer 216 having properties of the type discussed earlier in connection with layer 16. Barriers layers 214 and 216 can be incorporated into the cover sleeve in any convenient manner, such as but not limited to, coating portions 240 and 242 or positioning and securing the barrier layers to those portions of the sleeve. The barrier layer material can be applied to either the interior or exterior surface of the sleeve or, depending on the nature of the barrier material, the selected portions can be impregnated with the barrier layer material. It should be appreciated that depending on the nature of the barrier layer material, portions 240 and 242 might not be water permeable; however the remaining portions of cover sleeve 222 are water permeable.

It is contemplated that rather than being supplied with discrete lengths, the splint 10 can be rolled in a tape-like manner and stored in a resealable, air and moisture tight bag. In this manner, the required length splint can be cut from the tape with the remainder resealed in the bag for further use.

The present invention will now be illustrated by the following specific non-limiting examples.

Tests were conducted to evaluate the strength of the splints of the present invention by measuring the force required to deflect the splints. The mat configurations tested are shown in Table 1. All the mats were constructed from glass fibers.

TABLE 1

| Sample | Construction | Weight (kg/m$^2$)/(oz/ft$^2$) |
|---|---|---|
| A[1] | needled random continuous fibers | 0.61/2 |
| B[2] | needled random continuous fibers | 0.92/3 |
| C[3] | needled random continuous fibers | 0.92/3 |
| D[4] | needled random continuous fibers | 1.52/5 |
| E[5] | random continuous fibers needled with unidirectional strand | 1.71/5.6 |
| F[6] | random continuous fibers needled with unidirectional strand | 2.38/7.8 |
| G[7] | random continuous fibers needled with unidirectional strand | 1.02/3.35 |

[1]similar to ZETAMAT 1020 mat commercially available from PPG Industries with a binder that also included corn starch, a fungicide and an additional epoxy functional silane.
[2]similar to ZETAMAT 1030 mat commercially available from PPG Industries with a binder that also included corn starch, a fungicide and an additional epoxy functional silane.
[3]ZETAMAT 1030 mat commercially available from PPG Industries, Inc.
[4]ZETAMAT 1050 mat commercially available from PPG Industries, Inc.
[5]ZETAMAT 2056 mat commercially available from PPG Industries, Inc.
[6]ZETAMAT 2078 mat commercially available from PPG Industries, Inc.
[7]PPG mat product code 529340056 commercially available from PPG Industries, Inc.

The mats were cut into 7.3 m (8 yard) lengths having a 10.2 cm (4 inch) width. The mat was then run through a resin bath and sealed in an air and moisture tight foil pouch. In order to ensure that the mat was thoroughly impregnated with the resin, the sealed pouch was rotated every 24 hours in a room where the temperature was cycled between 32.2–35° C. (90–95° F.) for 12 hour, followed by room temperature for 12 hours. This cycle was continues for 4–5 days. The pouch was then opened, the mat was cut to the desired length, and the splint was assembled. More specifically, the mat was positioned between a polyethylene closed cell foam layer and a polyethylene plastic layer and the subassembly was enclosed within a stockinette. The stockinette was stitched closed and the splint was sealed in an air and moisture tight foil pouch. The splints were tested within 1 to 2 days.

The resin used to impregnate the mats was a urethane prepolymer comprising 56.01 wt % Mobay MONDUR CD isocyanate, 41.77 wt % Mobay MONTRONAL E9109 polyol, 1.78 wt % Texaco TEXACATT DMDEE catalyst, 0.34 wt % Dow Corning DC-1500 antiformer and 0.10 wt % benzoyl chloride.

The following test method was used for determining the load required to deflect the splint a predetermined distance.

Step 1—A bucket was filled with water having a temperature of about 74–78° F. (23.3–25.6° C.). The splint package was then opened and the splint was immersed in the water for 8–10 seconds.

Step 2—The splint was removed from the bucket, squeezed without wringing to remove the water, and laid out flat. Any ridges in the splint were smoothed out.

Step 3—Measured from the time the splint was initially immersed in water, the amount of time it took for the splint to set-up, i.e. begin to harden, was determined.

Step 4—6 minutes after initial immersion, the splint was clamped in a fixed position by a receiver with 7.62 cm (3 inches) extending out from the receiver for a deflection.

Step 5—The free end of the splint, i.e. the non-clamped end, was deflected upward a distance of 19.05 mm (0.75 inches) using an Instrom Series 1130 material testing system and the load required to deflect the free end was measured using a Dylan model no. 96-2564-10 load cell after the deflection was maintained for 30 seconds.

Step 6—Step 5 was repeated after either 60 minutes or 90 minutes from the initial immersion of the splint in the water on a different portion of the splint. It is believed that there is no significant difference between the deflection load after 60 minutes and the deflection load after 90 minutes.

Table 2 shows the results of the deflection test for splints incorporating the sample mats as well as the test results for two commercially available splint assemblies that use multilayered knitted fabrics rather than a mat as disclosed in the present invention. Control 1 was a fiber glass splint system available from Zimmer, Inc., Warsaw, IN that included 6 layers of knitted fabric, and Control 2 was a casting splint available from Smith and Nephew, Inc. Charlette, N.C. that included 7 layers of knitted fabric. The set-up time for each sample splint and the control splints was between about 3 and about 3.5 minutes. All the splints tested were 10.2 cm (4 inches) wide, except for Control 2 which was 10.8 cm (4.25 inches) wide.

TABLE 2

| Sample | Resin Content (g) | Load to deflect splint 19.05 mm after 6 minutes (N) | Load to deflect splint 19.05 mm after 60 minutes (N) | Load to deflect splint 19.05 mm after 90 minutes (N) |
|---|---|---|---|---|
| A | 30 | 32.47 | 92.07 | — |
| B | 50 | 103.19 | 184.15 | — |
| C | 25 | 73.39 | — | 104.53 |
| D | 33 | 108.98 | — | 154.35 |
| E | 40 | 222.40 | — | 274.89 |

TABLE 2-continued

| Sample | Resin Content (g) | Load to deflect splint 19.05 mm after 6 minutes (N) | Load to deflect splint 19.05 mm after 60 minutes (N) | Load to deflect splint 19.05 mm after 90 minutes (N) |
| --- | --- | --- | --- | --- |
| F | 42 | 327.82 | — | 384.75 |
| G | 60 | 135.22 | 355.40 | — |
| Control 1 | | 67.61 | | 102.75 |
| Control 2 | | 159.68 | | 231.30 |

Based on the above, although not limiting in the present invention, it is preferred that the splint 10 as disclosed herein have a deflection load of at least about 66.7 newtons (about 15 lbs.), preferably at least about 89 newtons (about 20 lbs.), and most preferably at least about 111.2 newtons (about 25 lbs.). As used herein, the term "deflection load" means the load required to deflect a splint 10 a distance of 19.05 mm (0.75 inches), 60 minutes after the resin matrix system has been activated. The deflection is measured at a distance of 7.62 cm (3 inches) from a fixed portion of the splint, and the load being measured after the deflection has been held for 30 seconds, as taught above.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

We claim:

1. An orthopedic splint for temporarily supporting an injured body limb, comprising:
    a non-woven mat at least partially impregnated with a curable resin matrix material;
    a first resin impermeable layer extending along at least a portion of at least one major surface of the mat;
    a second resin impermeable layer extending along at least a portion of an opposing major surface of the mat; and
    a curing agent permeable cover surrounding the mat and the first and second resin impermeable layers.

2. The splint according to claim 1 wherein the mat comprises glass fibers at least partially coated with a coating that is compatible with the resin matrix material.

3. The splint according to claim 2 wherein the mat comprises a needled mat comprising randomly oriented continuous glass fibers.

4. The splint according to claim 3 wherein the resin matrix material comprises a moisture curable, ambient air dried resin matrix material, the mat has a weight, prior to resin impregnation, of between about 0.15 to about 2.44 kilograms per square meter, the first resin impermeable layer is a heat insulating layer, and the cover is a water permeable cover.

5. The splint according to claim 4 wherein the mat further comprises unidirectional continuous glass fibers.

6. The splint according to claim 2 wherein the mat comprises randomly oriented chopped glass fibers.

7. The splint according to claim 2 wherein the mat further comprises unidirectional continuous glass fibers.

8. The splint according to claim 1 wherein the resin matrix material comprises a moisture curable, ambient air dried resin matrix material.

9. The splint according to claim 8 wherein the resin matrix material comprises a water curable, isocyanate containing resin.

10. The splint according to claim 1 wherein the first and second resin impermeable layers each comprise at least one material independently selected from a group consisting of polyvinylchloride, polyethylene, polyester, polyether, ethylene vinyl acetate, polychloroprene, silicone rubber, polyolefins and polyurethane.

11. The splint according to claim 1 wherein the mat has a weight, prior to resin impregnation, of between about 0.15 to about 2.44 kilograms per square meter.

12. The splint according to claim 11 wherein the mat has a weight, prior to resin impregnation, of between about 0.31 to about 1.83 kilograms per square meter.

13. The splint according to claim 12 wherein the mat has a weight, prior to resin impregnation, of between about 0.61 to about 1.22 kilograms per square meter.

14. The splint according to claim 1 wherein the splint has a deflection load of at least about 66.7 newtons.

15. The splint according to claim 1 wherein the splint has a deflection load of at least about 89 newtons.

16. The splint according to claim 1 wherein the splint has a deflection load of at least about 111.2 newtons.

17. The splint according to claim 1 wherein the mat comprises at least two mat layers.

18. An orthopedic splint for temporarily supporting an injured body limb, comprising:
    a non-woven mat at least partially impregnated with a curable resin matrix material; and
    a curing agent permeable cover surrounding the mat, the cover comprising:
        a first portion which overlays at least a portion of a first major surface of the mat and provides a first resin impermeable barrier; and
        a second portion which overlays at least a portion of an opposing second major surface of the mat and provides a second resin impermeable barrier.

19. The splint according to claim 18 wherein the first resin impermeable barrier is a heat insulating barrier, the cover includes water permeable portions, the resin matrix material comprises a moisture curable, ambient air dried resin matrix material, and the mat comprises a needled mat comprising randomly oriented continuous glass fibers and has a weight, prior to resin impregnation, of between about 0.15 to about 2.44 kilograms per square meter.

20. The splint according to claim 19 wherein the splint has a deflection load of at least about 66.7 newtons.

21. An orthopedic splint for temporarily supporting an injured body limb, comprising:
    a non-woven mat at least partially impregnated with a curable resin matrix material;
    a resin impermeable layer extending along at least a portion of at least one major surface of the mat; and
    a curing agent permeable cover surrounding the mat and the resin impermeable layer, the cover comprising a portion which overlays at least a portion of an opposing second major surface of the mat and provides a resin impermeable barrier.

* * * * *